(12) United States Patent
Fienberg et al.

(10) Patent No.: US 10,916,414 B2
(45) Date of Patent: Feb. 9, 2021

(54) ION BEAM FOCUS ADJUSTMENT

(71) Applicant: IONpath, Inc., Menlo Park, CA (US)

(72) Inventors: Harris Fienberg, Redwood City, CA (US); David Stumbo, Pleasanton, CA (US); Michael Angelo, Menlo Park, CA (US); Rachel Finck, Menlo Park, CA (US)

(73) Assignee: IONpath, Inc., Menlo Park, CA (US)

( * ) Notice: Subject to any disclaimer, the term of this patent is extended or adjusted under 35 U.S.C. 154(b) by 0 days.

(21) Appl. No.: 16/257,135

(22) Filed: Jan. 25, 2019

(65) Prior Publication Data
US 2019/0228958 A1 Jul. 25, 2019

Related U.S. Application Data

(60) Provisional application No. 62/621,687, filed on Jan. 25, 2018.

(51) Int. Cl.
H01J 49/00 (2006.01)
G01N 33/68 (2006.01)
H01J 49/06 (2006.01)
G01N 33/58 (2006.01)

(52) U.S. Cl.
CPC .......... H01J 49/0068 (2013.01); G01N 33/58 (2013.01); G01N 33/6848 (2013.01); H01J 49/00 (2013.01); H01J 49/0004 (2013.01); H01J 49/067 (2013.01)

(58) Field of Classification Search
CPC ........ H01J 49/0068; H01J 37/00; H01J 37/02; H01J 37/252; H01J 2237/06358; H01J 2237/2448; H01J 2237/2516; H01J 2237/2806

USPC ................ 250/281, 282, 492.1, 492.2, 492.3
See application file for complete search history.

(56) References Cited

U.S. PATENT DOCUMENTS

| 5,532,090 | A | * | 7/1996 | Borodovsky | ......... | G03F 7/2022 |
| | | | | | | 430/322 |
| 5,850,083 | A | * | 12/1998 | Koikari | ................ | H01J 37/153 |
| | | | | | | 250/396 R |
| 2008/0210857 | A1 | * | 9/2008 | Felton | ................ | H01J 49/0004 |
| | | | | | | 250/282 |
| 2009/0179161 | A1 | * | 7/2009 | Ward | .................... | B82Y 10/00 |
| | | | | | | 250/492.21 |
| 2010/0001202 | A1 | * | 1/2010 | Matsuda | ................ | H01J 37/12 |
| | | | | | | 250/396 R |
| 2012/0061561 | A1 | * | 3/2012 | Antonov | ............ | H01J 49/0027 |
| | | | | | | 250/282 |

* cited by examiner

Primary Examiner — Jason L McCormack
(74) Attorney, Agent, or Firm — Fish & Richardson P.C.

(57) ABSTRACT

The disclosure features systems and methods that include: exposing a biological sample to an ion beam that is incident on the sample at a first angle to a plane of the sample by translating a position of the ion beam on the sample in a first direction relative to a projection of a direction of incidence of the ion beam on the sample; after each translation of the ion beam in the first direction, adjusting a focal length of an ion source that generates the ion beam; and measuring and analyzing secondary ions generated from the sample by the ion beam after adjustment of the focal length to determine mass spectral information for the sample, where the sample is labeled with one or more mass tags and the mass spectral information includes populations of the mass tags at locations of the sample.

15 Claims, 8 Drawing Sheets

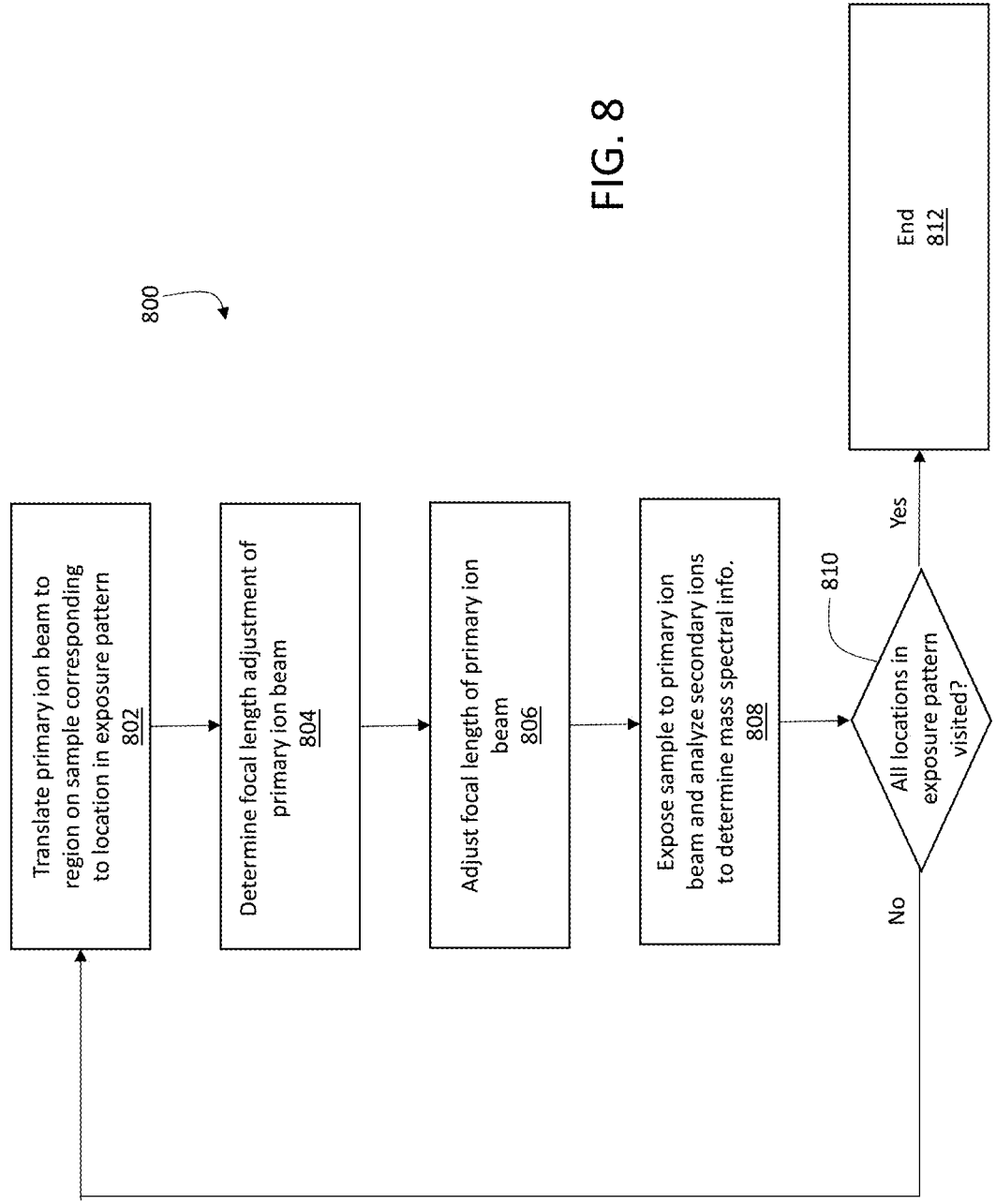

ION BEAM FOCUS ADJUSTMENT

CROSS-REFERENCE TO RELATED APPLICATIONS

This application claims priority to U.S. Provisional Application No. 62/621,687, filed on Jan. 25, 2018, the entire contents of which are incorporated herein by reference.

TECHNICAL FIELD

This disclosure relates to scanning of biological samples using an ion beam, and to determining mass spectrometry information for the samples based on ion beam exposure.

BACKGROUND

Immunohistochemistry methods have been used to visualize protein expression in biological samples such as tumor tissue biopsies. Such methods typically involve exposing a sample to antibodies coupled to fluorescent moieties or enzyme reporters that generate colored pigments. Analysis of spectral images of the tagged sample yields information that can be used to assess protein expression levels and co-expression events. A variety of samples can be analyzed using such methods, including formalin-fixed, paraffin-embedded tissue sections.

SUMMARY

This disclosure features multiplexed ion beam imaging methods for analyzing protein expression and other biological events and structures in biological samples. Samples are tagged with antibodies conjugated to mass tags such as lanthanide elements and then exposed to a beam of primary ions. The primary ions are incident on the sample and generate secondary ions based on the mass tags. Spatially- and mass-resolved analysis of the secondary ions from the sample can provide information about protein expression and other biological events at specific sample locations.

To enhance the yield of secondary ions from a sample, the sample can be tilted relative to the orientation of an incident primary ion beam. However, when the region of the sample exposed to the primary ion beam is sufficiently extended in a direction parallel to the axis of the primary ion beam, imaging artifacts arising from the tilted orientation of the sample can arise. Specifically, due to the tilted orientation, not all exposed portions of the sample may be located in the focal plane of the primary ion beam. This situation can lead to blurring and compromised spatial resolution in sample images, and may impede subsequent image analysis and information extraction.

This disclosure features methods and systems in which the focal length of an ion source is adjusted during scanning of the ion beam to ensure that exposed regions of a tilted sample remain at, or close to, a focal plane of the ion source. Focal length adjustment is performed based on the position of the ion beam relative to the sample. Depending upon the orientation of the ion beam relative to the sample, focal length adjustment can be performed for displacements of the ion beam from a reference position in one coordinate direction or in both coordinate directions.

In general, in a first aspect, the disclosure features methods that include: exposing a biological sample to an ion beam that is incident on the sample at a first angle to a plane of the sample by translating a position of the ion beam on the sample in a first direction relative to a projection of a direction of incidence of the ion beam on the sample; after each translation of the ion beam in the first direction, adjusting a focal length of an ion source that generates the ion beam; and measuring and analyzing secondary ions generated from the sample by the ion beam after adjustment of the focal length to determine mass spectral information for the sample, where the sample is labeled with one or more mass tags and the mass spectral information includes populations of the mass tags at locations of the sample.

Embodiments of the methods can include any one or more of the following features.

An angle between the first direction and the projection of the direction of incidence of the ion beam on the sample can be 20 degrees or less. The first direction and the projection of the direction of incidence of the ion beam on the sample can be approximately parallel.

Translating the position of the ion beam can include adjusting an angle of the ion beam relative to an axis of the ion source.

The methods can include translating the position of the ion beam on the sample in a second direction relative to the projection of the direction of incidence of the ion beam on the sample. An angle between the second direction and the projection of the direction of incidence of the ion beam on the sample can be 70 degrees or more. The second direction and the projection of the direction of incidence of ion beam on the sample can be approximately orthogonal.

The position of the ion beam can be translated across the sample in a two-dimensional exposure pattern. The two-dimensional exposure pattern can be a rectangular exposure pattern. A maximum length of the two-dimensional exposure pattern in the first direction can be at least 100 microns (e.g., at least 500 microns).

The first angle can be between 30 degrees and 60 degrees. The first angle can be approximately 45 degrees.

The methods can include adjusting the focal length of the ion source by adjusting a numerical aperture of the ion source. The methods can include adjusting the focal length of the ion source by adjusting a voltage applied to at least one electrode in the ion source.

The methods can include adjusting the ion source to reduce spherical aberration of the ion beam on the sample. The methods can include adjusting voltages applied to one or more electrodes in the ion source to reduce the spherical aberration of the ion beam on the sample.

The methods can include adjusting the ion source to compensate for curvature of a focal plane of the ion source. The methods can include adjusting voltages applied to one or more electrodes in the ion source to compensate for the curvature of the focal plane.

The methods can include adjusting the focal length of the ion source after at least some translations of the position of the ion beam in the second direction. The methods can include determining, after translating the position of the ion beam in the second direction, whether to adjust the focal length of the ion source based on a location of the ion beam on the sample.

Measuring and analyzing the secondary ions can include detecting at least some of the secondary ions emerging from the sample along a direction approximately orthogonal to the plane of the sample.

The one or more mass tags can include at least one type of antibody-conjugated lanthanide element, and the at least some of the secondary ions can include at least one type of lanthanide ion.

Embodiments of the methods can also include any of the other features disclosed herein, including features disclosed in connection with different embodiments, in any combination except as expressly stated otherwise.

In another aspect, the disclosure features systems that include an ion source configured to generate an ion beam, a stage positioned to support a biological sample, an ion detector configured to detect ions generated from the sample, and a controller connected to the ion source, the stage, and the ion detector, and configured so that during operation, the controller: (a) directs the ion source to expose the sample to the ion beam, where the ion beam is incident on the sample at a first angle to a plane of the sample, and where the controller directs the ion source to translate a position of the ion beam on the sample in a first direction relative to a projection of a direction of incidence of the ion beam on the sample; (b) adjusts a focal length of the ion source after each translation of the ion beam in the first direction; (c) receives a signal from the ion detector that includes information about secondary ions generated from the sample in response to the ion beam exposure after adjustment of the focal length; and (d) analyzes the signal to determine mass spectral information for the sample, where the sample is labeled with one or more mass tags and the mass spectral information includes populations of the mass tags at locations of the sample.

Embodiments of the systems can include any one or more of the following features.

An angle between the first direction and the projection of the direction of incidence of the ion beam on the sample can be 20 degrees or less. The first direction and the projection of the direction of incidence of the ion beam on the sample can be approximately parallel.

The controller can be configured to direct the ion source to translate the position of the ion beam on the sample by adjusting an angle of the ion beam relative to an axis of the ion source. The controller can be configured to direct the ion source to translate the position of the ion beam on the sample in a second direction relative to the projection of the direction of incidence of the ion beam on the sample. An angle between the second direction and the projection of the direction of incidence of the ion beam on the sample can be 70 degrees or more. The second direction and the projection of the direction of incidence of ion beam on the sample can be approximately orthogonal.

The controller can be configured to direct the ion source to translate the position of the ion beam across the sample in a two-dimensional exposure pattern. The two-dimensional exposure pattern can be a rectangular exposure pattern. A maximum length of the two-dimensional exposure pattern in the first direction can be at least 100 microns (e.g., at least 500 microns).

The first angle can be between 30 degrees and 60 degrees. The first angle can be approximately 45 degrees.

The controller can be configured to adjust the focal length of the ion source by adjusting a numerical aperture of the ion source. The controller can be configured to adjust the focal length of the ion source by adjusting a voltage applied to at least one electrode in the ion source.

The controller can be configured to adjust the ion source to reduce spherical aberration of the ion beam on the sample. The controller can be configured to adjust voltages applied to one or more electrodes in the ion source to reduce the spherical aberration of the ion beam on the sample.

The controller can be configured to adjust the ion source to compensate for curvature of a focal plane of the ion source. The controller can be configured to adjust voltages applied to one or more electrodes in the ion source to compensate for the curvature of the focal plane.

The controller can be configured to adjust the focal length of the ion source after at least some translations of the position of the ion beam in the second direction. The controller can be configured to determine, after the position of the ion beam has been translated in the second direction, whether to adjust the focal length of the ion source based on a location of the ion beam on the sample.

The ion detector can be configured to detect at least some of the secondary ions emerging from the sample along a direction approximately orthogonal to the plane of the sample. The one or more mass tags can include at least one type of antibody-conjugated lanthanide element, and the at least some of the secondary ions can include at least one type of lanthanide ion.

Embodiments of the systems can also include any of the other features disclosed herein, including features disclosed in connection with different embodiments, in any combination except as expressly stated otherwise.

In a further aspect, the disclosure features methods that include: exposing a first set of regions of a biological sample positioned in a sample plane to an ion beam from an ion source, where an axis of the ion source is aligned along a first direction inclined at a first angle relative to the sample plane, and where exposing the first set of regions includes translating a location of incidence of the ion beam on the sample along a second direction in the sample plane that is approximately orthogonal to a projection of the first direction onto the sample plane; translating the location of incidence of the ion beam on the sample along a third direction in the sample plane that is approximately parallel to the projection of the first direction onto the sample plane; adjusting a focal length of the ion source based on the translated location of incidence of the ion beam on the sample along the third direction; and, after adjusting the focal length, exposing a second set of regions of the biological sample to the ion beam, where exposing the second set of regions includes translating the location of incidence of the ion beam on the sample along the second direction in the sample plane, the biological sample is labeled with one or more mass tags, and exposing at least some of the first and second pluralities of regions to the ion beam generates secondary ions corresponding to the one or more mass tags.

Embodiments of the methods can include any one or more of the following features.

Translating the location of incidence of the ion beam on the sample along the third direction can include adjusting an angle of the ion beam relative to the axis of the ion source. The first angle can be between 30 degrees and 60 degrees.

Exposing the first and second sets of regions can include translating the location of incidence of the ion beam on the sample along the second direction over a length of 100 microns or more (e.g., over a length of 500 microns or more). Translating the location of incidence of the ion beam on the sample along the second direction can include adjusting an angle of the ion beam relative to the axis of the ion source.

The methods can include exposing additional sets of regions of the biological sample to the ion beam by: (a) translating the location of incidence of the ion beam on the sample along the third direction prior to exposing each additional set of regions; (b) adjusting the focal length of the ion source; and (c) exposing an additional set of regions of the biological sample to the ion beam, where exposing the additional set of regions includes translating the location of incidence of the ion beam on the sample along the second direction in the sample plane.

The first, second, and additional sets of regions can form a two-dimensional exposure pattern of the ion beam on the sample. A length of the exposure pattern measured in the third direction can be 100 microns or more (e.g., 500 microns or more).

The methods can include adjusting the focal length of the ion source by adjusting a numerical aperture of the ion source. The methods can include adjusting the focal length of the ion source by adjusting a voltage applied to at least one electrode in the ion source.

The methods can include adjusting the focal length of the ion source between exposing each one of the first set of regions to the ion beam and between exposing each one of the second set of regions to the ion beam.

The methods can include collecting at least some of the secondary ions and analyzing the secondary ions to obtain mass spectral information for the mass tags labeling the sample. Collecting and analyzing the at least some of the secondary ions can include detecting the at least some of the secondary ions emerging from the sample along a fourth direction that is approximately orthogonal to the sample plane.

The one or more mass tags can include at least one type of antibody-conjugated lanthanide element, and the at least some secondary ions can include at least one type of lanthanide ion.

Embodiments of the methods can also include any of the other features disclosed herein, including features disclosed in connection with different embodiments, in any combination except as expressly stated otherwise.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the subject matter herein, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

In general, method steps described herein and in the claims can be performed in any order, except where expressly prohibited or logically inconsistent. It should be noted that describing steps in a particular order does not mean that such steps must be performed in the described order. Moreover, the labeling of steps with identifiers does not impose an order on the steps, or imply that the steps must be performed in a certain sequence. To the contrary, the steps disclosed herein can generally be performed in any order except where noted otherwise.

The details of one or more embodiments are set forth in the accompanying drawings and the description below. Other features and advantages will be apparent from the description, drawings, and claims.

DESCRIPTION OF DRAWINGS

FIG. 8 is a flow chart showing a series of example steps for adjusting the focal length of a primary ion beam during scanning of the beam over a sample.

Like reference symbols in the various drawings indicate like elements.

DETAILED DESCRIPTION

(i) Introduction

Figure 1:
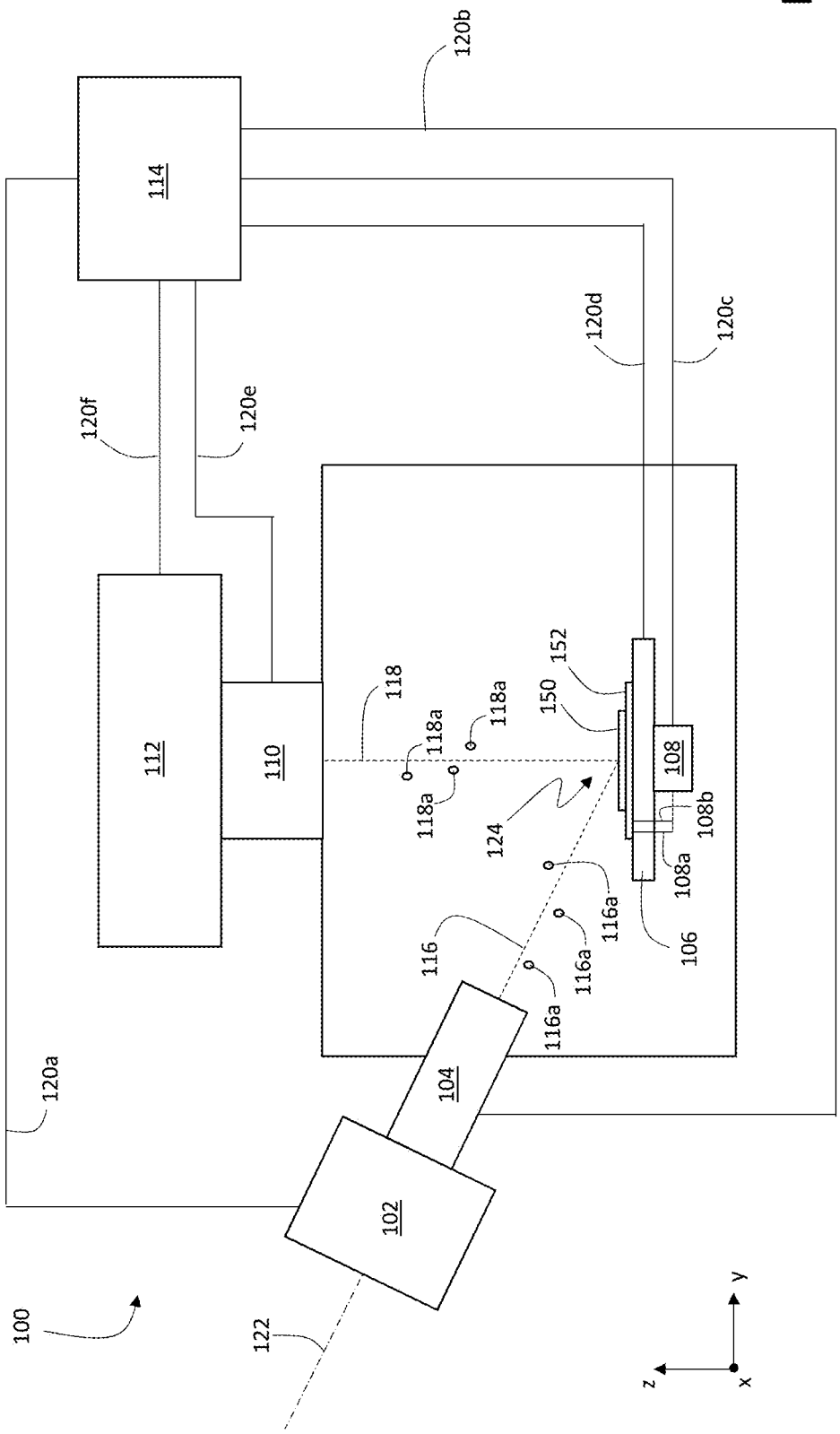
FIG. 1 is a schematic diagram of an example of a multiplexed ion beam imaging system.

Multiplexed visualization of protein expression and other biochemical moieties and structures allows researchers to identify important correlations between biological functional events. Visualization of protein expression can be used to assess malignancies in excised tissue samples as part of a diagnostic work-up, and in particular, to provide important information about signaling pathways and correlated structural development in tumor tissue.

Conventional multiplexed immunohistochemical techniques for visualizing protein expression typically rely on optical detection of fluorescence emission from a sample that has been labeled with multiple antibody-conjugated flurophores. The conjugated fluorophores bind specifically to corresponding antigens in the sample, and imaging of fluorescence emission from the sample is used to assess the spatial distribution of the fluorophores. For samples in which antigen concentrations are relatively low, signal amplification (e.g., using multivalent, enzyme-linked secondary antibodies) can be used to aid visualization. However, the use of signal amplification techniques can compromise quantitative information (e.g., antigen concentration information) that might otherwise be extracted from sample images.

In conventional multiplexed immunohistochemical visualization techniques, other constraints can also be encountered. Optical detection and separation of spectral signatures of multiple fluorophores is a complex problem, particularly where the fluorescence spectra of the fluorophores exhibit significant overlap. Without robust discrimination between spectral signatures of the fluorophores, important expression-related information is not uncovered. Further, such techniques often rely on primary antibodies generated in dissimilar host species. These factors can limit the utility of conventional multiplexed immunohistochemical visualization techniques for predictive biomarker development and clinical diagnostics.

This disclosure features methods for performing multiplexed visualization of antigens and other biochemical structures and moieties in biological samples using secondary ion mass spectrometry. Structure-specific antibodies are conjugated to specific mass tags, typically in the form of metallic elements (e.g., lanthanide elements). When a sample is exposed to the conjugated antibody-mass tag labels, the labels bind to corresponding antigens. Exposure of the labeled sample to a primary ion beam liberates secondary ions corresponding to the conjugated mass tags from the labeled sample. Performing spatially-resolved detection of the secondary ions that are generated from the sample allows direct visualization of the localization of specific antigens in the sample, and extraction of quantitative information (e.g., antigen concentration) as a function of spatial location. This information can be combined with other structural information (e.g., information about tumor margins, cell types/morphologies) to develop a detailed assessment of tumor viability and progression in the sample.

The methods disclosed herein, which are referred to as multiplexed ion beam imaging (MIBI) methods, can be used to resolve spatial distributions of relatively large numbers of mass tags applied to samples. For example, visual and quantitative assessment of up to 100 different mass tags in a single sample are possible. Depending upon the nature of the mass tags applied to the sample, sensitivities in the parts-per-billion range can be achieved with a dynamic range of approximately $10^5$. Imaging resolution is typically comparable to optical microscopy at high magnification.

The following sections of this disclosure describe examples of systems for multiplexed ion beam imaging, components of the systems, and methods for performing multiplexed ion beam imaging and sample preparation.

(ii) Multiplexed Ion Beam Imaging Systems

FIG. 1 is a schematic diagram showing an example system 100 for multiplexed ion beam imaging. System 100 includes an ion beam source 102, ion beam optics 104, a stage 106, a voltage source 108, ion collecting optics 110, and a detection apparatus 112. Each of these components is connected to a controller 114 via signal lines 120a-120f. During operation of system 100, controller 114 can adjust operating parameters of each of ion beam source 102, ion beam optics 104, stage 106, voltage source 108, ion collecting optics 110, and detection apparatus 112. Further controller 114 can exchange information with each of the foregoing components of system 100 via signal lines 120a-120f.

During operation, ion beam source 102 generates an ion beam 116 that includes a plurality of primary ions 116a. Ion beam 116 is incident on a sample 150 that is positioned on stage 106. Optionally, in certain embodiments, voltage source 108 applies an electrical potential to a substrate 152 that supports sample 150. Primary ions 116a in ion beam 116 interact with sample 150, generating secondary ions 118a as a secondary ion beam 118. Secondary ion beam 118 is collected by ion collecting optics 110 and directed into detection apparatus 112. Detection apparatus 112 measures one or more ion counts corresponding to secondary ions 118a in secondary ion beam 118 and generates electrical signals corresponding the measured ion counts. Controller 114 receives the measured electrical signals from detection apparatus 112 and analyzes the electrical signals to determine information about secondary ions 118a and sample 150.

Controller 114 can adjust a wide variety of different operating parameters of the various components of system 100, and can transmit information (e.g., control signals) and receive information (e.g., electrical signals corresponding to measurements and/or status information) from the components of system 100. For example, in some embodiments, controller 114 can activate ion beam source 102 and can adjust operating parameters of ion beam source 102, such as an ion current of ion beam 116, a beam waist of ion beam 116, and a propagation direction of ion beam 116 relative to central axis 122 of ion beam source 102. In general, controller 114 adjusts the operating parameters of ion beam source 102 by transmitting suitable control signals to ion beam source 102 via signal line 120a. In addition, controller 114 can receive information from ion beam source 102 (including information about the ion current of ion beam 116, the beam waist of ion beam 116, the propagation direction of ion beam 116, and various electrical potentials applied to the components of ion beam source 102) via signal line 120a.

Ion beam optics 104 generally include a variety of elements that use electric fields and/or magnetic fields to control attributes of ion beam 116. In some embodiments, for example, ion beam optics 104 include one or more beam focusing elements that adjust a spot size of ion beam 116 at a location of incidence 124 of ion beam 116 on sample 150. In certain embodiments, ion beam optics 104 include one or more beam deflecting elements that deflect ion beam 116 relative to axis 122, thereby adjusting the location of incidence 124 of ion beam 116 on sample. Ion beam optics 104 can also include a variety of other elements, including one or more apertures, extraction electrodes, beam blocking elements, and other elements that assist in directing ion beam 116 to be incident on sample 150.

Controller 114 can generally adjust the properties of any of the foregoing elements via suitable control signals transmitted via signal line 120b. For example, controller 114 can adjust the focusing properties of one or more beam focusing elements of ion beam optics 104 by adjusting electrical potentials applied to the beam focusing elements via signal line 120b. Similarly, controller 114 can adjust the propagation direction of ion beam 116 (and the location of incidence 124 of ion beam 116 on sample 150) by adjusting electrical potentials applied to the beam deflection elements via signal line 120b. Further, controller 114 can adjust positions of one or more apertures and/or beam blocking elements in ion beam optics 104, and adjust electrical potentials applied to extraction electrodes in ion beam optics 104, via suitable control signals transmitted on signal line 120b. In addition to adjusting properties of ion beam optics 104, controller 114 can receive information from various components of ion beam optics 104, including information about electrical potentials applied to the components of ion beam optics 104 and/or information about positions of the components of ion beam optics 104.

Stage 106 includes a surface for supporting sample 150 (and substrate 152). In general, stage 106 can be translated in each of the x-, y-, and z-coordinate directions. Controller 114 can translate stage 106 in an of the above directions by transmitting control signals on signal line 120d. To effect a translation of the location of incidence 124 of ion beam 116 on sample 150, controller 114 can adjust one or more electrical potentials applied to deflection elements of ion beam optics 104 (e.g., to deflect ion beam 116 relative to axis 122), adjust the position of stage 106 via control signals transmitted on signal line 120d, and/or adjust both deflection elements of ion beam optics 104 and the position of stage 106. In addition, controller 114 receives information about the position of stage 106 transmitted along signal line 120d.

In some embodiments, system 100 includes a voltage source 108 connected to substrate 152 via electrodes 108a and 108b. When activated by controller 114 (via suitable control signals transmitted on signal line 120c), voltage source 108 applies an electrical potential to substrate 152. The applied electrical potential assists in the capture of secondary ion beam 118 from sample 150, as the electrical potential repels secondary ions 118a, causing the secondary ions to leave sample 150 in the direction of ion collecting optics 110.

As shown in FIG. 1, sample 150 is typically a relatively planar sample that extends in the x- and/or y-coordinate directions and has a thickness measured in the z-coordinate direction. The support surface of stage 106 likewise extends in the x- and y-coordinate directions.

Secondary ion beam 118 consisting of a plurality of secondary ions 118a is captured by ion collecting optics 110. In general, ion collecting optics 110 can include a variety of electric and magnetic field-generating elements for deflecting and focusing secondary ion beam 118. In addition, ion collecting optics 100 can include one or more apertures, beam blocking elements, and electrodes. As discussed above in connection with ion beam optics 104, controller 114 can adjust electrical potentials applied to each of the components of ion collecting optics 110 via suitable control signals transmitted on signal line 120e. Controller 114 can also adjust the positions of apertures, beam blocking elements, and other movable components of ion collecting optics 110 by transmitting control signals on signal line 120e. In addition, controller 114 can receive information about operating parameters (e.g., voltages, positions) of various components of ion collecting optics 110 on signal line 120e.

Ion collecting optics 110 direct secondary ion beam 118 into detection apparatus 112. Detection apparatus 112 measures ion counts or currents corresponding to the various types of secondary ions 118a in secondary ion beam 118, and generates output signals that contain information about the measured ion counts or currents. Controller 114 can adjust various operating parameters of detection apparatus 112, including maximum and minimum ion count detection thresholds, signal integration times, the range of mass-to-charge (m/z) values over which ion counts are measured, the dynamic range over which ion counts are measured, and electrical potentials applied to various components of detection apparatus 112, by transmitting suitable control signals over signal line 120f.

Controller 114 receives the output signals from detection apparatus that include information about the measured ion counts or currents on signal line 120f. In addition, controller 114 also receives operating parameter information for the various components of detection apparatus 112 via signal line 120f, including values of the various operating parameters discussed above.

Detection apparatus 112 can include a variety of components for measuring ion counts/currents corresponding to secondary ion beam 118. In some embodiments, for example, detection apparatus 112 can correspond to a time-of-flight (TOF) detector. In certain embodiments, detection apparatus 112 can include one or more ion detectors such as Faraday cups, which generate electrical signals when ions are incident on their active surfaces. In some embodiments, detection apparatus 112 can be implemented as a multiplying detector, in which incident ions enter an electron multiplier where they generate a corresponding electron burst. The electron burst can be detected directly as an electrical signal, or can be incident on a converter that generates photons (i.e., an optical signal) in response to the incident electrons. The photons are detected with an optical detector which generates the output electrical signal.

As discussed above, controller 114 is capable of adjusting a wide variety of operating parameters of system 100, receiving and monitoring values of the operating parameters, and receiving electrical signals containing information about secondary ions 118a (and other species) generated from sample 150. Controller 114 analyzes the electrical signals to extract the information about secondary ions 118a and other species. Based on the extracted information, controller 114 can adjust operating parameters of system 100 to improve system performance (e.g., m/z resolution, detection sensitivity) and to improve the accuracy and reproducibility of data (e.g., ion counts) measured by system 100. Controller 114 can also execute display operations to provide system users with images of sample 150 that show distributions of various mass tags within sample 150, and storage operations to store information relating to the distributions in non-volatile storage media.

(iii) Sample Preparation

In general, the methods and systems disclosed are compatible with a wide variety of biological samples. Typically, sample 150 is a tissue sample extracted from a human or animal patient. Sample 150 can correspond to a sample of tumor tissue excised during biopsy, or another type of tissue sample retrieved via another invasive surgical or non-invasive procedure.

In some embodiments, sample 150 corresponds to a formalin-fixed, paraffin-embedded tissue sample. Such samples are commonly prepared during histological workup of biopsied tissue from cancer tumors and other anatomical locations.

In certain embodiments, sample 150 corresponds to an array of single cells on a substrate. The array can be naturally occurring, and correspond to a regularly occurring, ordered arrangement of cells in a tissue sample. Alternatively, the array of cells can be a product of sample preparation. That is, the sample can be prepared by manual or automated placement of individual cells on substrate 152 (e.g., in a series of wells or depressions formed in substrate 152) to form the cell array.

Figure 2:
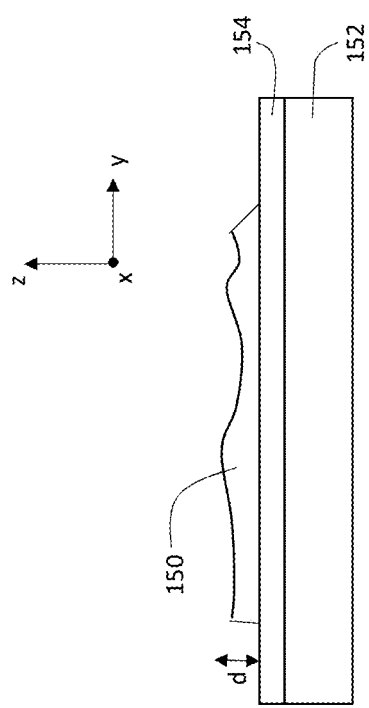
FIG. 2 is a schematic cross-sectional diagram of a sample on a substrate.

FIG. 2 is a schematic cross-sectional diagram of sample 150 on substrate 152. Positioned between substrate 152 and sample 150 in FIG. 2 is an optional coating 154. When present, coating 154 can be electrically connected to voltage source 108 via electrodes 108a and 108b, as shown in FIG. 1.

Substrate 152 is typically implemented as a microscope slide or another planar support structure, and can be formed from a variety of materials including various types of glass, plastics, silicon, and metals.

Coating 154, if present, is typically formed of one or more metallic elements, or one or more non-metallic compounds of relatively high conductivity. Examples of metallic elements used to form coating 154 include, but are not limited to, gold, tantalum, titanium, chromium, tin, and indium. In certain embodiments, coating 154 can be implemented as multiple distinct coating layers, each of which can be formed as a separate layer of a metallic element or a separate layer of a relatively high conductivity, non-metallic compound.

As shown in FIG. 2, sample 150 is approximately planar and extends in the x- and/or y-coordinate directions, and has a thickness d measured in the z-coordinate direction. Depending upon the method of preparation of sample 150, the sample can have an approximately constant thickness d across the planar extent of the sample parallel to the x-y coordinate plane. Alternatively, many real samples corresponding to excised tissue have non-constant thicknesses d across the planar extent of the sample parallel to the x-y coordinate plane. In FIG. 2, sample 150—which is shown in cross-section—has a non-constant thickness d measured in the z-coordinate direction.

In general, the thickness d of sample 150 depends upon the method by which sample 150 is obtained and processed prior to mounting on substrate 152. Certain samples, for example, are microtome-sliced from larger blocks of tissue, and can have relatively constant thicknesses. As another example, certain samples are obtained directly via excision, and can have variable thicknesses. The thickness d of sample 150 can be from 500 nm to 500 microns (e.g., from 1 micron to 300 microns, from 1 micron to 200 microns, from 1 micron to 100 microns, from 10 microns to 100 microns).

In some embodiments, substrate 152 can also include one or more additional coating materials to facilitate adhesion of sample 150 to substrate 152. Where no coating 154 is present, the one or more additional coating materials can be applied directly to substrate 150, such that the additional coating materials form a layer positioned between sample 150 and substrate 152. Where coating 154 is present, the one or more additional coating materials can be applied atop coating 154, for example, such that the additional coating materials form a layer positioned between coating 154 and sample 150. Suitable additional coating materials to facilitate adhesion of sample 150 include, but are not limited to, poly-l-lysine.

Figure 3:
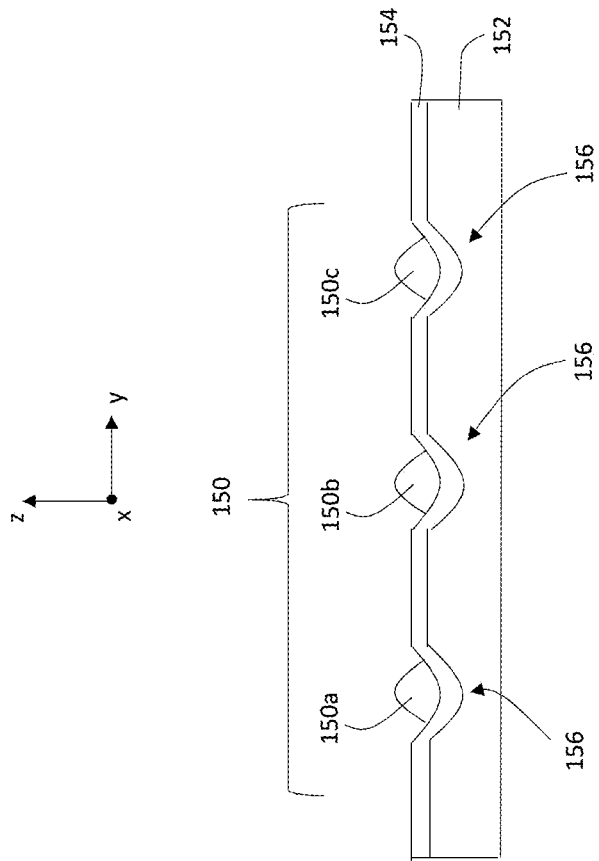
FIG. 3 is a schematic cross-sectional diagram of a sample with one or more conformal coating layers.

FIG. 3 shows a schematic cross-sectional diagram of another sample 150 positioned on a substrate 152. Substrate 152 optionally includes one or more conformal coating layers 154 as discussed above. In addition, substrate 152 includes an array of wells 156 corresponding to depressions formed in a surface of substrate 152. Each of the wells 156 contains a portion 150a-150c of sample 150. In general, while substrate 152 includes three wells 156 containing three separate portions 150a-150c of sample 150 in FIG. 3, more generally substrate 152 can include any number of wells 156, and sample 150 can be apportioned among any one or more of the wells 156.

Wells 156 (and the portions of sample 150 distributed among wells 156) can generally arranged in a variety of patterns in substrate 152. For example, wells 156 can form a linear (i.e., one dimensional) array in substrate 152. Alternatively, wells 156 can be distributed along one dimension in the plane of substrate 152, with irregular spacings between some or all of the wells.

As another example, wells 156 can form a two-dimensional array in substrate 152, with regular spacings between adjacent wells in directions parallel to both the x- and y-coordinate directions in the plane of substrate 152. Alternatively, in either or both of the directions parallel to the x- and y-coordinate directions in the plane of substrate 152, at least some of wells 156 can be spaced irregularly.

Where wells 156 form a two-dimensional array in substrate 152, the array can take a variety of forms. In some embodiments, the array of wells 156 can be a square or rectangular array. In certain embodiments, the array can be a hexagonal array, a polar array having radial symmetry, or another type of array having geometrical symmetry in plane of substrate 152.

As discussed above, each of the portions 150a-150c of sample 150 can include one or more cells. During sample preparation, each portion 150a-150c can be dispensed or positioned in a corresponding well 156 of substrate 152 to form sample 150. For example, each portion 150a-150c of sample 150 can be dispensed into a corresponding well 156 as a suspension of cells in a liquid medium, and the liquid medium subsequently removed (e.g., by washing or heating) to leave the cells in each well 156.

In general, to facilitate various biochemical structural analyses of sample 150 such as protein expression, sample 150 is labeled with multiple mass tags. When sample 150 is exposed to primary ion beam 116, the mass tags are ionized and liberated from sample 150. The ionized mass tags correspond to secondary ions 118a and form secondary ion beam 118 emerging from sample 150. Analysis of the secondary ions 118a present in secondary ion beam 118 as a function of the location of incidence 124 of ion beam 116 on sample 150 by controller 114 yields a wealth of information about the biochemical structure of sample 150 at each of the locations of incidence 124.

A variety of different mass tags can be used in the systems and methods disclosed herein. In some embodiments, the mass tags correspond to metallic elements, and more specifically, to lanthanide elements. Lanthanide elements suitable for use as mass tags include, for example, lanthanum, neodymium, samarium, gadolinium, erbium, ytterbium, and dysprosium.

To apply the mass tags to sample 150, each of the mass tags is conjugated to a specific antibody that selectively binds to an antigen receptor in sample 150. In practice, solutions of each of the antibody-conjugated mass tags are prepared, and then sample 150 is labeled by exposing sample 150 to each of the mass tag solutions. Sample 150 is typically exposed to multiple mass tag solutions sequentially and/or in parallel so that sample 150 can be labelled with multiple, distinct mass tags.

To prepare suitable mass tag labeling solutions, various methods can be used. For example, primary antibodies conjugated to metallic elemental tags (e.g., lanthanide metal elements) can generally be prepared 100 μg at a time using the MaxPAR antibody conjugation kit (available from DVS Sciences, Toronto, Canada) according to the manufacturer's recommended protocol. After conjugation, the labeled antibodies can be diluted in Candor PBS Antibody Stabilization solution (available from Candor Bioscience GmbH, Wangen, Germany) to a concentration of approximately 0.4 mg/mL, and stored long term at approximately 4° C. For preparation of samples consisting of arrays of cells, as shown in FIG. 3, cells in suspension can be augmented with surface marker antibodies and incubated at room temperature for approximately 30 minutes. Following incubation, cells can be washed twice with the mass tag labeling solutions to label the cells. Individual aliquots of the labeled cells, diluted in PBS to yield a desired concentration of cells per unit volume (e.g., approximately $10^7$ cells/mL), can then be placed in wells 156 and allowed to adhere for approximately 20 minutes. The adhered cells can then be gently rinsed with PBS, fixed for approximately 5 minutes in PBS with 2% glutaraldehyde, and rinsed twice with deionized water. Samples can then be dehydrated via a graded ethanol series, air dried at room temperature, and stored in a vacuum dessicator for at least 24 hours prior to analysis.

For preparation of intact tissue samples, such as samples obtained from biopsy, tissue samples can be mounted on substrate 152. Following mounting, the samples can be baked at approximately 65° C. for 15 minutes, deparaffinized in xylene (if obtained from FFPE tissue blocks), and rehydrated via a graded ethanol series. The samples are then immersed in epitope retrieval buffer (10 mM sodium citrate, pH 6) and placed in a pressure cooker (available from Electron Microscopy Sciences, Hatfield, Pa.) for approximately 30 minutes. Subsequently, the samples are rinsed twice with deionized water and once with wash buffer (TBS, 0.1% Tween, pH 7.2). Residual buffer solution can be removed by gently touch the samples with a lint free tissue. The samples are then incubated with blocking buffer for approximately 30 minutes (TBS, 0.1% Tween, 3% BSA, 10% donkey serum, pH 7.2).

The blocking buffer is then removed and the samples are labeled overnight with the mass tag labeling solutions at 4° C. in a humidified chamber. Following labeling, the samples are rinsed twice in wash buffer, postfixed for approximately 5 minutes (PBS, 2% glutaraldehyde), rinsed in deionized water, and stained with Harris hematoxylin for 10 seconds. The samples are then dehydrated via graded ethanol series, air dried at room temperature, and stored in a vacuum dessicator for at least 24 hours prior to analysis.

It should be understood that the above preparative steps are merely provided as examples of methods for sample preparation, and that modifications to the above sequences of steps also yield samples that are suitably labeled with mass tags and prepared for MIBI analysis. In particular, modifications to be above sequences of preparative steps can be undertaken based on the nature of the samples (e.g., the type of tissue to which the samples correspond).

(iv) Sample Scanning

To perform multiplexed ion beam imaging following suitable labeling of sample 150 with multiple mass tags, primary ion beam 116 is directed to multiple different locations of incidence 124 on sample 150. At each location 124, primary ion beam 116 generates secondary ions 118a that correspond to the antibody-conjugated mass tags bound to sample 150 at that location. The secondary ions 118a— which form secondary ion beam 118—are measured and analyzed to determine spatially resolved information about the biochemical structure of sample 150.

A variety of different primary ion beams 116 generated by ion source 102 can be used to expose sample 150. In some embodiments, for example, primary ion beam 116 consists of a plurality of oxygen ions (O$^-$). For example, ion source 102 can be implemented as an oxygen duoplasmatron source, which generates primary ion beam 116.

To obtain spatially resolved information from sample 150, primary ion beam 116 is translated across sample 150 to multiple different locations of incidence 124. The multiple different locations of incidence form a two-dimensional exposure pattern of primary ion beam 116 in the plane of sample 150 (i.e., in a plane parallel to the x-y plane). In general, a wide variety of different exposure patterns can be used.

Figure 4A:
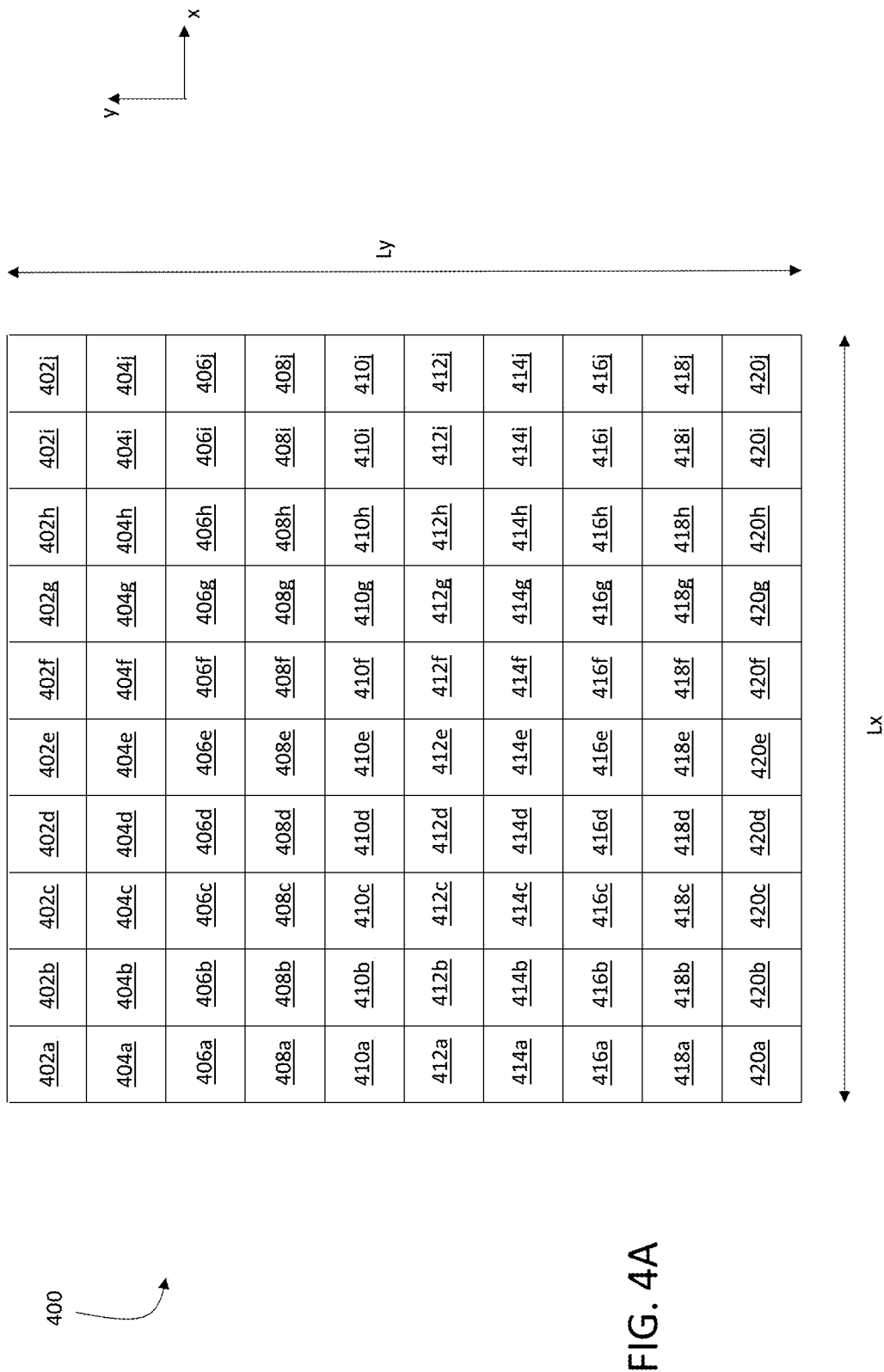
FIG. 4A is a schematic diagram showing an example of an ion beam exposure pattern on a sample.

In some embodiments, for example, the exposure pattern corresponds to a square or rectangular array of locations of incidence 124 of primary ion beam 116 on sample 150. FIG. 4A is a schematic diagram showing a square array of locations of incidence 124 of primary ion beam 116 on sample 150, forming a square exposure pattern 400 on sample 150. Each row of exposure pattern 400 includes 10 distinct locations of incidence 124 of primary ion beam 116 on sample 150, spaced along the x-coordinate direction. Each column of exposure pattern 400 includes 10 distinct locations of incidence 124 of primary ion beam 116 on sample 150, spaced along the y-coordinate direction. In total, exposure pattern 400 includes 100 distinct locations of incidence 124 of primary ion beam 116.

In general, each row and column of exposure pattern 400 can include any number of distinct locations of incidence 124 of primary ion beam 116 on sample 150. For example, in some embodiments, each row and/or column of exposure pattern 400 includes 10 or more (e.g., 20 or more, 30 or more, 50 or more, 100 or more, 200 or more, 300 or more, 500 or more, 1000 or more) distinct locations of incidence 124 of primary ion beam 116.

To expose sample 150 to primary ion beam 116 according to exposure pattern, the different locations of incidence 124 constituting exposure pattern 400 can generally be visited in any order by primary ion beam 116. In some embodiments, however, the different locations of incidence 124 are visited in certain sequences. For example, the square exposure pattern 400 in FIG. 4A can be implemented such that primary ion beam 116 is scanned along each row of the exposure pattern in sequence. After visiting each location of incidence 124 in a single row in sequence (e.g., by translating primary ion beam 116 parallel to the x-coordinate direction), primary ion beam 116 is translated parallel to the y-coordinate direction to the next row in exposure pattern 400, and then visits each location of incidence 124 in the next row in sequence.

This example sequence of exposures corresponds to a pattern of raster-scanning of primary ion beam 116 on sample 150. As shown in FIG. 4A, locations 402a-402j are each visited in sequential order by primary ion beam 116, followed by locations 404a-404j in sequential order, and so on in sequence until the final row of locations 420a-420j is visited in sequential order.

Exposure pattern 400 includes a total of 100 distinct locations of incidence of primary ion beam 116 on sample 150. More generally, however, exposure pattern 400 can include any number of distinct locations of incidence of primary ion beam 116. In certain embodiments, for example, exposure pattern 400 includes 25 or more (e.g., 50 or more, 100 or more, 200 or more, 500 or more, 1000 or more, 5000 or more, 10000 or more, 20000 or more, 30000 or more, 50000 or more, 100000 or more, 200000 or more, 500000 or more) distinct locations of incidence of primary ion beam 116 on sample 150.

A maximum dimension of exposure pattern 400 measured in a direction parallel to the x-coordinate direction is Lx, and a maximum dimension of exposure pattern 400 measured in a direction parallel to the y-coordinate direction is Ly. In general, Lx and Ly are selected as desired according to the spatial dimensions of the portion of sample 150 to be analyzed. For example, in some embodiments, Lx and Ly can each independently be 25 microns or more (e.g., 50 microns or more, 100 microns or more, 200 microns or more, 300 microns or more, 400 microns or more, 500 microns or more, 700 microns or more, 1.0 mm or more, 1.5 mm or more, 2.0 mm or more, 2.5 mm or more, 3.0 mm or more, 5.0 mm or more).

Figure 4C:
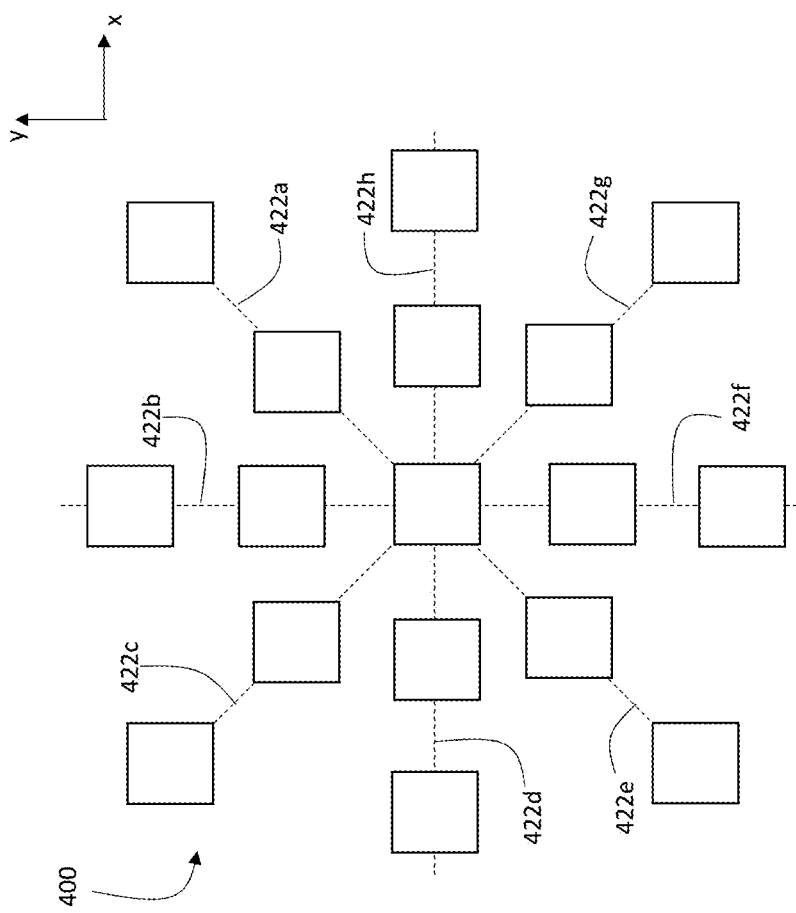
FIG. 4C is a schematic diagram showing an example of a radial ion beam exposure pattern.
Figure 4B:
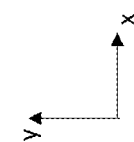
FIG. 4B is a schematic diagram showing another example of an ion beam exposure pattern on a sample in which rows of the exposure pattern are offset.

Exposure pattern 400 in FIG. 4A is a square pattern. More generally, however, the exposure pattern formed by the set of locations of incidence 124 of primary ion beam 116 on sample 150 need not be square or rectangular. Two-dimensional exposure patterns having a variety of different shapes and spacings between locations of incidence of primary ion beam 116 can be implemented. FIG. 4B is a schematic diagram showing an exposure pattern 400 in which rows of the exposure pattern are offset spatially in the x-direction, forming an offset array. FIG. 4C is a schematic diagram showing a radial exposure pattern 400 in which individual locations of incidence of primary ion beam 116 are exposed in sequence along radial lines 422a-422h.

Returning to FIG. 4A, when sample 150 is exposed to primary ion beam 116 according to exposure pattern 400, the exposure can be implemented based on a single execution of exposure pattern 400 or based on multiple executions of exposure pattern 400. In other words, in some embodiments, sample 150 is exposed to primary ion beam 116 by directing primary ion beam 116 to visit each location in exposure pattern 400 once. In certain embodiments, sample 150 is exposed to primary ion beam 116 by directing primary ion beam 116 to visit each location in exposure pattern 400 multiple times. Typically, for example, after primary ion beam 116 has visited each location in exposure pattern 400 once, primary ion beam 116 follows a second exposure sequence in which the beam visits the locations in exposure pattern 400 a second time. Subsequent exposure sequences can be implemented in which primary ion beam 116 repeats the sequence of exposures defined by exposure pattern 400 as many times as desired.

In general, the accuracy and reproducibility of the ion counts/currents measured by detection apparatus 112 depends on number of secondary ions 118*a* generated by the interaction between primary ion beam 116 and sample 150. The number of secondary ions generated at each location of incidence 124 of primary ion beam 116 is in turn a function of the total primary ion dose at each location. As the primary ion dose increases, all other factors being held constant, the number of secondary ions generated also increases. As discussed above, the total dose of primary ions at each location of incidence 124 can be delivered via a single exposure to primary ion beam 116 at each location, or via multiple exposures to primary ion beam 116 at each location (i.e., by repeating exposure pattern 400).

In summary, as used herein, the term "exposure pattern"—examples of which are represented schematically by exposure patterns 400 in FIGS. 4A-4C—refers to the set of spatial locations of incidence of primary ion beam 116 on sample 150, as well as the set of dwell times (also referred to as exposure times), ion doses, ion beam currents, and other exposure parameters associated with each of the spatial locations of incidence of primary ion beam 116 on sample 150. In some embodiments, controller 114 maintains information corresponding to the exposure pattern in a volatile and/or non-volatile memory unit. During operation of system 100, controller 114 can modify the exposure pattern—by modifying the set of locations of incidence of primary ion beam 116 associated with the exposure pattern, and/or by modifying any of the exposure parameters associated with the set of spatial locations—in response to ion counts/currents measured by detection apparatus 112, and/or to adjust performance-related metrics for system 100 such as signal resolution, signal-to-noise ratio, and data reproducibility and/or accuracy.

In some embodiments, to control the location of incidence 124 of primary ion beam 116 on sample 150, controller 114 translates stage 106 in the x- and y-coordinate directions via control signals transmitted on signal line 120*d*. With primary ion beam 116 directed to a static location, motion of stage 106 in the x- and y-coordinate directions effects translations of sample 150 in the x- and y-coordinate directions relative to the location of primary ion beam 116, thereby moving the location of incidence 124 of primary ion beam 116.

Figure 5:
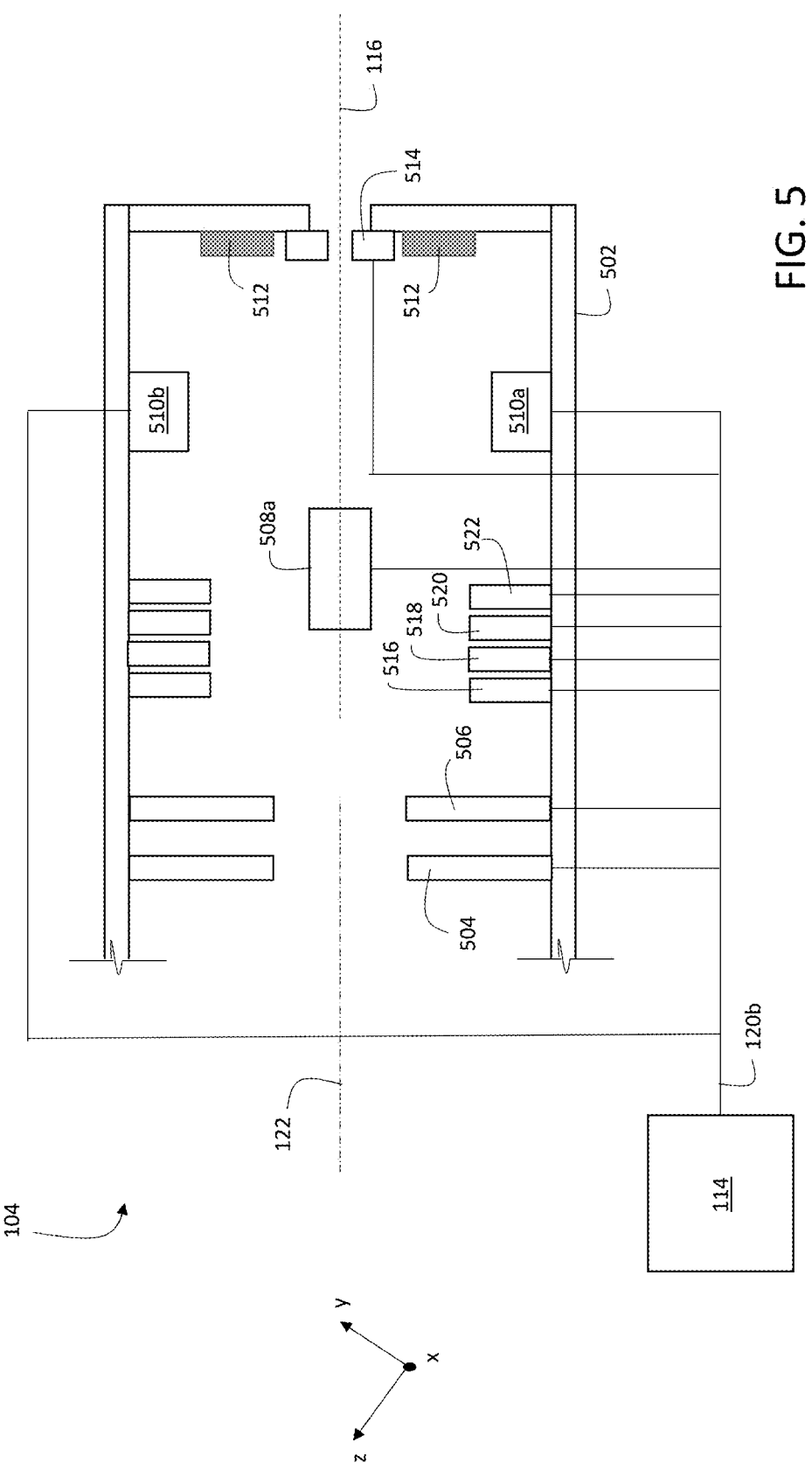
FIG. 5 is a schematic diagram showing an example of a portion of ion beam optics for a multiplexed ion beam imaging system.

Alternatively, or in addition, in certain embodiments controller 114 adjusts one or more elements of ion beam optics 104 to translate the location of primary ion beam 116 on sample 150. FIG. 5 is a schematic diagram showing an example of a portion of ion beam optics 104. Ion beam optics 104 include a housing 502 that encloses a variety of components, including focusing elements 504 and 506 (implemented as annular electrostatic lenses), a first pair of deflection electrodes (only one of which, electrode 508*a*, is shown in FIG. 5 due to the perspective of the figure), and a second pair of deflection electrodes 510*a* and 510*b*. Ion beam optics 104 also include beam blocking elements 512.

Controller 114 is electrically connected to focusing elements 504 and 506, to the first pair of deflection electrodes (shown via a connection to electrode 508*a* in FIG. 5), and to the second pair of deflection electrodes 510*a* and 510*b*, via signal line 120*b*. Controller 114 adjusts electrical potentials applied to each of the elements to which it is connected by transmitting appropriate signals on signal line 120*b*.

During operation of system 100, primary ion beam 116 enters ion beam optics 104 through an aperture (not shown in FIG. 5) in housing 502, propagating nominally along central axis 122 of ion beam optics 104. By applying suitable electrical potentials to annular focusing elements 504 and 506, controller 114 adjusts the focal position of primary ion beam 116 along axis 122.

Controller 114 can adjust the location of incidence 124 of primary ion beam 116 on sample 150 by adjusting electrical potentials applied to the first and second pairs of deflection electrodes via control signals transmitted along signal line 120*b*. For example, by adjusting the electrical potentials applied to the first pair of deflection electrodes (electrode 508*a* and a cooperating second electrode not shown in FIG. 5), primary ion beam 116 is deflected in a direction parallel to the x-coordinate direction. Thus, to scan primary ion beam 116 in a direction parallel to the x-coordinate direction in an exposure pattern, controller 114 adjusts the electrical potentials applied to the first pair of deflection electrodes.

Similarly, by adjusting the electrical potentials applied to the second pair of deflection electrodes, 510*a* and 510*b*, a component of the resulting deflection of primary ion beam 116 is parallel to the y-coordinate direction. Accordingly, to scan primary ion beam 116 in a direction parallel to the y-coordinate direction in an exposure pattern, controller 114 adjusts the electrical potentials applied to the second pair of deflection electrodes.

To prevent primary ion beam 116 from being incident on sample 150, controller 114 can adjust the electrical potentials applied to either or both pairs of deflection electrodes to cause primary ion beam 116 to be intercepted by a beam blocking element. For example, by applying suitable electrical potentials to electrodes 510*a* and 510*b*, primary ion beam 116 can be deflected such that the beam is blocked by beam blocking elements 512 in ion beam optics 104. Beam blocking elements can also be positioned external to ion beam optics 104, and the electrical potentials applied to deflection electrodes adjusted to steer primary ion beam 116 to be incident on the external beam blocking elements.

(v) Focal Length Adjustment

Sample images that are acquired using the methods described above can be visualized in various ways. In many applications, two or more images are overlaid to facilitate visualization of different sample features in a correlative manner. Images can also be analyzed to detect certain image features (e.g., cellular features such as nuclei, cell walls, and organelles), and manipulated using various algorithms (including, but not limited to, linear and nonlinear algorithms for operations such as stretching and alignment. All of these operations benefit from sample images that are well-focused across the entire image. In contrast, when edges or other features of such images are blurred or captured at low resolution, software-based manipulation of such images is made more difficult.

As shown in FIG. 4A, in some embodiments, primary ion beam 116 can be scanned over a relatively large exposure region on the surface of sample 150. If ion beam optics 104 are adjusted such that primary ion beam 116 is focused to a reference location that is coincident with the center of the exposure pattern in FIG. 4A, then absent further focal length adjustment, when primary ion beam 116 is displaced significantly from the reference location (e.g., toward the edges of the exposure pattern in FIG. 4A), primary ion beam 116 is not focused at its location of incidence 124 on the surface of sample 150. As a result, image information obtained from location 124 can be blurred and/or poorly resolved.

Defocusing of primary ion beam 116 as a function of the location of incidence 124 is further exacerbated by the angular orientation of primary ion beam 116 relative to the surface of sample 150. As shown in FIG. 1, primary ion beam 116 can be oriented at an angle relative to the normal to the surface of sample 150 upon which primary ion beam 116 is incident. The "tilted" orientation of primary ion beam 116 relative to sample 150 is useful for various reasons. An important reason for using such a tilted orientation is to increase production of secondary ions 118a from sample 150. It has been observed that the yield of secondary ions 118a is a function of the angular orientation of primary ion beam 116 relative to the surface of sample 150. In general, as the angle of primary ion beam 116 relative to the normal to the surface of sample 150 increases, the secondary ion yield also increases. Accordingly, in some embodiments, primary ion beam 116 is incident on the surface of sample 150 at a non-normal angle.

Another reason for orienting primary ion beam 116 in such a manner is to reduce backscattering of primary ions from beam 116 into detection apparatus 112. As shown in FIG. 1, due to the orientation of primary ion beam 116 relative to sample 150, primary ions that collide with and are scattered from the surface of sample 150 are scattered in a variety of directions, most of which are not along the direction of the surface normal to sample 150. As a result, most of the scattered primary ions do not enter detection apparatus 112, and therefore do not interfere with measured signals of interest from secondary ions 118a. As the angle between primary ion beam 116 and the normal to the sample surface increases, scattering of primary ions along the direction of the surface normal is reduced.

Figure 6:
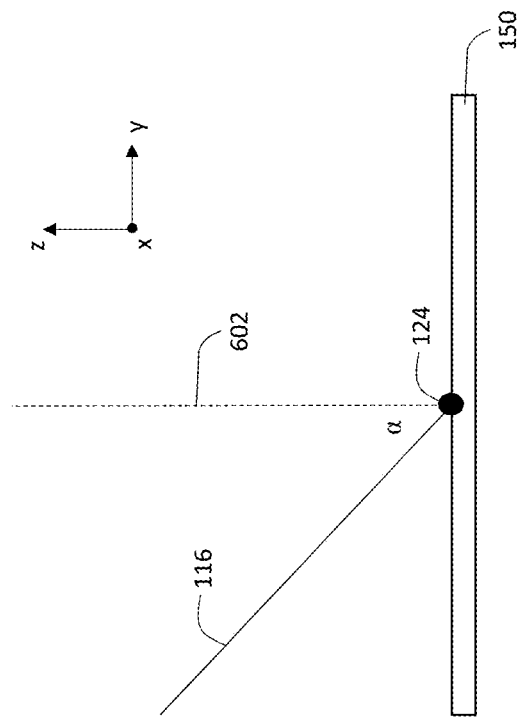
FIG. 6 is a schematic diagram showing an example of a primary ion beam incident at an angle on a surface of a sample.

The relative orientation between primary ion beam 116 and sample 150 is shown in FIG. 6. In FIG. 6, sample 150 is positioned in the x-y coordinate plane, and primary ion beam 116 is scanned over the surface of sample 150 in an exposure pattern in the x-y plane. Surface normal 602, which is orthogonal to the surface of sample 150 on which primary ion beam 116 is incident, is oriented in a direction parallel to the z-axis.

As discussed above, to increase the yield of secondary ions 118a and reduce the number of scattered primary ions that are detected by detection apparatus 112, primary ion beam 116 is tilted in the y-z plane and inclined at an angle α relative to surface normal 602. In general, primary ion beam 116 is not significantly tilted in the x-z plane. In other words, when the location of incidence 124 of primary ion beam 116 corresponds to a typical reference location (e.g., at the center of an exposure pattern on the surface of sample 150), primary ion beam 116 propagates in the y-z plane, with no significant component of propagation in the x-z plane.

In general, the angle of inclination α can be selected as desired to adjust the yield of secondary ions 118a and reduce detection of backscattered primary ions. In some embodiments, for example, α is 10 degrees or more (e.g., 20 degrees or more, 30 degrees or more, 35 degrees or more, 40 degrees or more, 45 degrees or more, 50 degrees or more, 55 degrees or more, 60 degrees or more, 70 degrees or more, 80 degrees or more, 85 degrees or more, 88 degrees or more, 89 degrees or more). In certain embodiments, α is between 10 degrees and 85 degrees (e.g., between 20 degrees and 85 degrees, between 20 degrees and 80 degrees, between 20 degrees and 70 degrees, between 30 degrees and 70 degrees, between 30 degrees and 60 degrees). In some embodiments, α is between 42 degrees and 48 degrees (i.e., approximately 45 degrees).

Referring to FIGS. 1, 4A, and 5, to direct primary ion beam 116 to different locations along the x-direction of exposure pattern 400, controller 114 adjusts the electrical potential applied to deflection electrode 508a (and its cooperating electrode not shown in FIG. 5), thereby deflecting primary ion beam 116 in a direction parallel to the x-direction. Deflecting primary ion beam 116 in this manner causes an angular displacement of primary ion beam 116 from axis 122 by at most a few degrees, depending upon the magnitude of $L_x$, the maximum dimension of exposure pattern 400 in the x-direction. Relatively minor angular displacements of such a magnitude typically do not result in significant defocusing of primary ion beam 116 for translations of the beam in the x-direction.

However, the situation is different for translations in the y-direction. To translate primary ion beam 116 along the y-direction of exposure pattern 400, controller 114 adjusts the electrical potentials applied to deflection electrodes 510a and 510b, thereby deflecting primary ion beam 116 such that a component of the deflection occurs in the y-direction. However, because primary ion beam 116 is already inclined at a significant angle α relative to surface normal 602, deflecting primary ion beam 116 by adjusting electrodes 510a and 510b can result in significant defocusing of primary ion beam 116 at different locations along the y-direction of exposure pattern 400.

Figure 7:
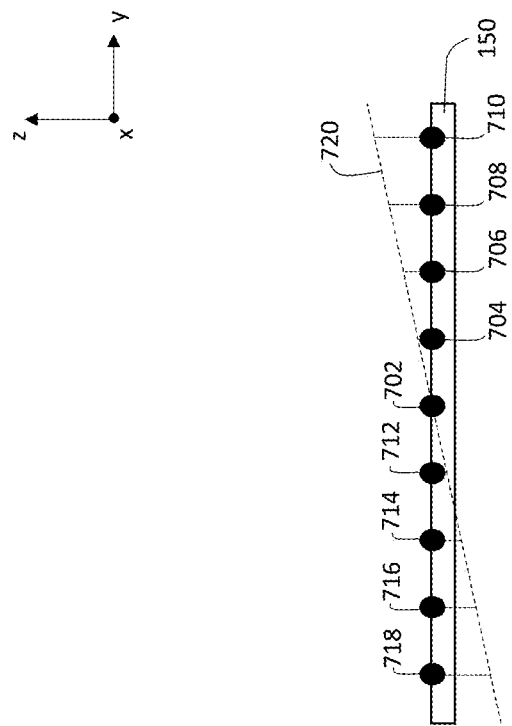
FIG. 7 is a schematic diagram showing multiple locations of incidence of a primary ion beam on a surface of a sample.

The defocusing of primary ion beam 116 along the y-direction is shown in FIG. 7, which is a schematic diagram illustrating a set of locations of incidence of primary ion beam 116 on sample 150. The locations of incidence 702, 704, 706, 708, 710, 712, 714, 716, and 718 correspond to a "column" of locations of incidence in an exposure pattern and are displaced from one another in the y-direction, but are aligned in the x-direction.

Location 702 is at the center of the exposure pattern. Ion source 102 and ion beam optics 104 are adjusted so that when primary ion beam 116 is incident on the surface of sample 150 at location 702, the focus of primary ion beam 116 coincides with the surface of sample 150 (or more generally, with any desired plane parallel to the surface of sample 150 and displaced from the sample surface in the z-direction).

Due to the angle of inclination α, as primary ion beam 116 is displaced from location 702 to locations 704, 706, 708, and 710—each of which is successively further from location 702 in the y-direction—the focal position of primary ion beam 116 is displaced from the surface of sample 150 due to the successively longer path length traveled by primary ion beam 116 to reach the sample surface. The successively longer path lengths are the result of the angle of inclination α. As α increases, so too does the defocusing of primary ion beam 116 as a function of displacement from location 702 along the y-direction.

Line 720 in FIG. 7 shows the actual locations of focus of primary ion beam 116 as a function of displacement from location 702 along the y-direction. For each of locations 704, 706, 708, and 710, the focal position of primary ion beam 116 is located above the surface of sample 150.

For locations 712, 714, 716, and 718, which are each displaced from location 702 in the opposite direction (i.e., the −y direction), the situation is reversed. As primary ion beam 116 is successively deflected to each of these locations, the path length traveled by the primary ion beam to reach sample 150 is successively shorter due to the angle of inclination α. As a result, for each of locations 712, 714, 716, and 718, the focal position of primary ion beam 116 is located below the surface of sample 150.

To compensate at least partially for defocusing of primary ion beam 116 among different locations in an exposure pattern on sample 150, controller 114 is configured to adjust the focus of primary ion beam 116 as the beam is scanned across sample 150. FIG. 8 is a flow chart 800 showing a series of example steps implemented by controller 114 to adjust the focal length of primary ion beam 116 during scanning. In a first step 802, controller 114 translates primary ion beam 116 to a region on the sample corresponding to a location in an exposure pattern. For example, referring to FIG. 4A, the region can correspond to any of the locations defined in exposure pattern 400.

Next, in step 804, controller 114 determines the focal length adjustment of the primary ion beam based on the location selected in step 802. In some embodiments, the focal length adjustment is determined based on the displacement in the y-direction of primary ion beam 116 from a reference location on the surface of sample 150 at which the focus of primary ion beam 116 is coincident with the surface of sample 150 (or with a plane parallel to the surface and displaced in a direction parallel to the z-direction). Referring to FIG. 7, with location 702 taken as the reference location, the focal length adjustment can be determined by controller 114 for a location such as location 704 based on the distance between locations 704 and 702, measured in the y-direction. In general, this distance is known to controller 114 from the exposure pattern, which specifies the distances between exposure locations.

As discussed above, defocusing is generally more strongly pronounced for displacements along the y-direction of primary ion beam 116 due to the angle of inclination α. As a result, focal length adjustments can be based only on the displacement of primary ion beam 116 from a reference location in the y-direction. However, in certain embodiments, controller 114 can be configured to perform focal length adjustments based on displacements of primary ion beam 116 from a reference location in both the x- and y-directions. Information about the displacement of primary ion beam 116 along both the x- and y-directions from a reference location is available to controller 114 from the exposure pattern, as discussed above.

To determine the focal length adjustment, controller 114 can refer to previously measured calibration information. Such information can include, for example, information about electrical potentials that can be applied to focusing elements 504 and 506 to adjust the focal length of primary ion beam 116 based on its location within the exposure pattern. Where focal length adjustment is performed only for displacements of primary ion beam 116 in the y-direction from a reference location, the information can include electrical potentials that can be applied for various displacements along the y-direction. In effect, the calibration information corresponds to a one-dimensional "map" of corrective electrical potentials as a function of displacement in the y-direction.

Where focal length adjustment is performed for displacements of primary ion beam 116 in both the x- and y-directions, the calibration information can effectively correspond to a two-dimensional map of corrective electrical potentials for each location in the exposure pattern, as a function of displacement in both the x- and y-directions.

In addition, or as an alternative, controller 114 can determine the focal length adjustment by first determining the change in path length of primary ion beam 116 due to displacement of primary ion beam 116 from the reference location on the sample. The change in path length can be estimated by controller 114 based on the angle of inclination α, the displacement of primary ion beam 116 along the y-direction (and along the x-direction as well, if adjustment for defocusing is to occur for such displacements), and other geometrical features describing the incidence of primary ion beam 116 on sample 150.

After the change in path length relative to the path length corresponding to incidence at the reference location has been determined, controller 114 then determines suitable electrical potentials to apply to focusing elements 504 and 506 to adjust the focal length of primary ion beam 116 to account for the change in path length. The determination of suitable electrical potentials can be based, for example, on a set of default potentials corresponding to the reference location, as well as information about the magnitudes of changes in potentials required to change the focal length of primary ion beam 116 by known amounts. Controller 114 uses this information to determine suitable corrections to the electrical potentials applied to focusing elements 504 and 506 to account for the change in path length of primary ion beam 116 due to deflection of the beam away from the reference location.

Next, in step 806, the focal length of primary ion beam 116 is adjusted by controller 114 based on the focal length adjustment determined in step 804. As discussed above, the focal length adjustment effectively corresponds to electrical potentials (or changes to electrical potentials) applied to focusing elements (e.g., elements 504 and 506) of ion optics 104 and/or ion source 102. Controller 114 applies the corrected electrical potentials to perform the focal length adjustment.

Then, in step 808, controller 114 exposes the sample to primary ion beam 116 with the focal length of the beam adjusted, generating secondary ions 118a. The secondary ions are detected by detection apparatus 112 and the measured signals from detection apparatus 112 are analyzed by controller 114 to determine mass spectral information about sample 150. Various aspects of this process have been described above.

In step 810, controller 114 determines whether all regions on the sample corresponding to the locations in the exposure pattern have been exposed. If so, the procedure terminates at step 812. If not, control returns to step 802 and controller 114 translates primary ion beam 116 to a new region of the sample corresponding to a different location in the exposure pattern.

As discussed above, in certain embodiments, focal length adjustment of primary ion beam 116 is performed by controller 114 only for displacements of primary ion beam 116 from a reference location that occur in a direction parallel to the y-direction. Because of the angle of incidence α, displacements along the y-direction typically result in more significant defocusing of the beam than displacements along the x-direction.

Restricting focal length adjustments to only y-direction displacements can provide an important advantage. Typically, adjusting the focal length of primary ion beam 116 is relatively slow as it involves adjusting the electrical potentials applied to focusing elements 504 and 506. When the exposure pattern includes a large number of locations, adjusting the focal length of primary ion beam 116 for each location is time-consuming and can significantly increase the time required to obtain a suitable set of mass spectral information for sample 150. By adjusting the focal length only after displacements in the y-direction, a considerable reduction in measurement time can be realized.

A further reduction in measurement time can be realized by scanning primary ion beam 116 across sample 150 along the length of each "row" of the exposure pattern in the x-direction before displacing the primary ion beam in the y-direction to the next row of the exposure pattern. By scanning the primary ion beam in such a manner, the x-direction effectively corresponds to the "fast" scanning direction and the y-direction corresponds to the "slow" scanning direction. Displacing primary ion beam 116 in this fashion minimizes the number of displacements in the y-direction and, consequently, the number of focal length adjustments of primary ion beam 116 performed by controller 114. As a result, a reduction in measurement time (relative to displacement patterns involving more interleaved displacements in the x- and y-directions) can be realized.

Such considerations are particularly important when the maximum dimensions of the exposure pattern in the x- and/or y-direction are relatively large (e.g., $L_x$ and/or $L_y$ are 100 microns or more, 200 microns, or more, 500 microns or more, or even more). Large exposure patterns can include hundreds or thousands of locations of incidence of the primary ion beam on the sample. Exposing the sample at each of the locations—and in some cases multiple times at each location—is already time-consuming. By scanning the sample such that the number of displacements of the primary ion beam in the "slow" direction is minimized (or reduced), the total measurement time for large exposure patterns does not become too large.

In the foregoing discussion, for purposes of clarity, primary ion beam 116 was inclined in the y-z plane, and the exposure pattern on the surface of the sample—as shown for example in FIG. 4A—included locations forming an array extending the x- and y-directions. More generally, however, the locations in the exposure pattern do not necessarily form an array aligned with the x- and y-coordinate directions.

Figure 9:
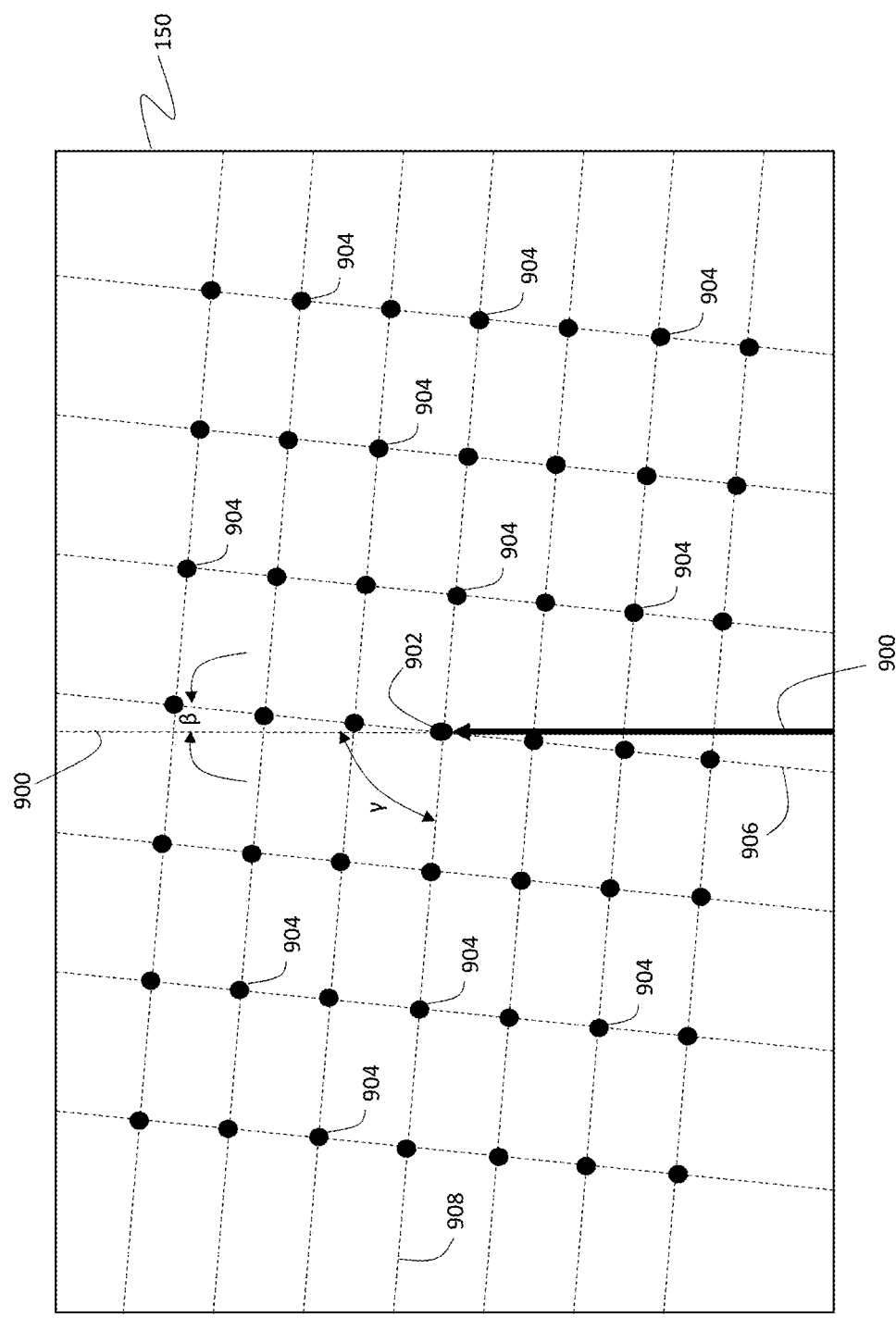
FIG. 9 is a schematic diagram showing a top view of a sample and multiple locations of incidence of a primary ion beam on the sample.

FIG. 9 is a schematic diagram showing a top view of a sample 150. Primary ion beam 116 propagates in the y-z plane and is inclined at an angle $\alpha$ relative to a surface normal of sample 150, as described above. A projection 900 of a direction of incidence of primary ion beam 116 at reference location 902 within an exposure pattern is also shown. The exposure pattern in FIG. 9 consists of reference location 902 and additional locations 904, which form an orthogonal array of locations on sample 150. The locations extend along directions 906 and 908.

In FIG. 9, direction 906 is oriented at an angle $\beta$ to the y-axis (i.e., to the direction of projection 900) and direction 908 is oriented at an angle $\gamma$ to the y-axis. That is, direction 906 corresponds to the "slow" scanning direction of the exposure pattern, while direction 908 corresponds to the "fast" scanning direction of the exposure pattern. The discussion above applies to circumstances in which primary ion beam 116 is scanned across the surface of sample 150 according to an exposure pattern that is rotated relative to the x- and y-directions as shown in FIG. 9. That is, focal length adjustments can be performed after displacements along only direction 906, or after displacements along either or both of directions 906 and 908.

In some embodiments, $\beta$ is relatively small, such as 20 degrees or less (e.g., 15 degrees or less, 10 degrees or less, 5 degrees or less). $\beta$ can even be sufficiently small (e.g., 3 degrees or less, 2 degrees or less, 1 degree or less, or even zero), such that direction 906 is approximately parallel to the y-direction.

In some embodiments, $\gamma$ is relatively large, such as 70 degrees or more (e.g., 75 degrees or more, 80 degrees or more, 85 degrees or more). $\gamma$ can even be sufficiently large (e.g., 87 degrees or more, 88 degrees or more, 89 degrees or more, or even 90 degrees), such that direction 908 is approximately orthogonal to the y-direction.

In the foregoing discussion, controller 114 adjusted the focal length of primary ion beam 116 by changing electrical potentials applied to focusing elements (e.g., focusing elements 504 and 506) in ion optics 104 and/or ion source 102. In certain embodiments, adjustments to the focal length of primary ion beam 116 can also involve adjusting the numerical aperture of primary ion beam 116. Adjusting the numerical aperture of an ion beam changes the beam's depth of focus. In particular, as the numerical aperture increases, the depth of focus decreases and the ion beam can be focused to a region that is thinner in a direction parallel to the direction of propagation of the ion beam.

In some embodiments, ion beam optics 104 include an adjustable aperture 514 as shown in FIG. 5. Aperture 514 is connected to controller 114 via signal line 120b and controller 114 can increase or decrease the diameter of aperture 514 via suitable control signals transmitted along signal line 120b. To increase the numerical aperture of primary ion beam 116 and shorten the depth of focus, controller 114 increases the diameter of aperture 514. In contrast, to reduce the numerical aperture and increase the depth of focus of primary ion beam 116, controller 114 reduces the diameter of aperture 514.

Changing the depth of focus of primary ion beam 116 has the effect of implementing "fine" adjustments to the focal length of the beam, where direct adjustments to the focal length (e.g., via elements 504 and 506) might be considered "coarse" adjustments to the focal length. In certain embodiments, controller 114 uses one or the other (or a combination) of coarse and fine adjustments of the focal length of primary ion beam 116 to account for displacements of the beam from a reference location in an exposure pattern. For example, fine adjustments of the focal length can be used for displacements in the x-direction only, while coarse adjustments (or a combination of fine and coarse adjustments) can be used for displacements in the y-direction (or the x- and y-directions).

In some embodiments, in addition to performing focal length adjustment of primary ion beam 116, controller 114 is configured to adjust various elements of ion source 102 and/or ion beam optics 104 to correct for other aberrations. For example, in certain embodiments, controller 114 is configured to correct for one or more aberrations including, but not limited to, spherical aberration, coma, distortion, field curvature, and chromatic aberration.

To implement such corrections, referring to FIG. 5, ion beam optics 104 can include a plurality of ion optical lens elements (shown as four elements, 516, 518, 520, and 522, but more generally including any number of such elements), each of which is connected via signal line 102b to controller 114. To correct for aberrations, controller 114 applies suitable electrical potentials to one or more of the lens elements. Various aspects and features associated with correcting aberrations in electron optical systems are disclosed, for example, in Rose et al., "Aberration Correction in Electron Microscopy," *Proc. IEEE Particle Accelerator Conference*, pp. 44-48 (2005), the entire contents of which are incorporated by reference herein. Similar considerations apply to ion optical systems.

By implementing optical elements for aberration correction in ion beam optics 104, more inexpensive ion lenses can be used in ion beam optics 104 which reduces the overall cost of system 100. Typically, more inexpensive lenses are not as well corrected for various types of aberrations. However, if such corrections are implemented via other elements in ion beam optics 104, the use of inexpensive lenses is more viable.

(vi) Hardware and Software Implementations

As discussed above, any of the steps and functions described herein can be executed by controller 114. In general, controller 114 can include a single electronic processor, multiple electronic processors, one or more integrated circuits (e.g., application specific integrated circuits), and any combination of the foregoing elements. Software- and/or hardware-based instructions are executed by controller 114 to perform the steps and functions discussed herein. Controller 114 can include a data storage system (including memory and/or storage elements), at least one input device, and at least one output device, such as a display. Each set of software-based instructions, embodied as a software program stored on a tangible, non-transient storage medium (e.g., an optical storage medium such as a CD-ROM or DVD, a magnetic storage medium such as a hard disk, or a persistent solid state storage medium) or device, can be implemented in a high-level procedural or object-oriented programming language, or an assembly or machine language.

OTHER EMBODIMENTS

A number of embodiments have been described. Nevertheless, it will be understood that various modifications may be made without departing from the spirit and scope of the disclosure. Accordingly, other embodiments are within the scope of the following claims.

What is claimed is:

1. A method, comprising:
translating a position of an ion beam that is incident on a biological sample at a first angle to a plane of the sample from a first location to a second location on the sample, the translation comprising displacing the ion beam in a first direction relative to a projection of a direction of incidence of the ion beam on the sample, and in a second direction relative to the projection of the direction of incidence of the ion beam on the sample, wherein an angle between the first direction and the projection of the direction of incidence of the ion beam on the sample is 20 degrees or less and an angle between the second direction and the projection of the direction of incidence of the ion beam on the sample is 70 degrees or more;
adjusting a focal length of an ion source that generates the ion beam based on the displacement in the first direction but not on the displacement in the second direction; and
after adjustment of the focal length of the ion source, exposing the sample at the second location to the ion beam, and measuring and analyzing secondary ions generated from the sample by the ion beam to determine mass spectral information for the sample,
wherein the sample is labeled with one or more mass tags and the mass spectral information comprises populations of the mass tags at locations of the sample.

2. The method of claim 1, wherein translating the position of the ion beam comprises adjusting an angle of the ion beam relative to an axis of the ion source.

3. The method of claim 1, wherein the position of the ion beam is translated across the sample in a two-dimensional exposure pattern, wherein a maximum length of the two-dimensional exposure pattern in the first direction is at least 100 microns, and wherein a maximum length of the two-dimensional exposure pattern in the first direction is at least 500 microns.

4. The method of claim 1, further comprising adjusting the focal length of the ion source by adjusting a numerical aperture of the ion source.

5. The method of claim 1, further comprising adjusting the ion source to reduce spherical aberration of the ion beam on the sample by adjusting voltages applied to one or more electrodes in the ion source.

6. The method of claim 1, further comprising adjusting the ion source to compensate for curvature of a focal plane of the ion source by adjusting voltages applied to one or more electrodes in the ion source.

7. The method of claim 3, further comprising adjusting the focal length of the ion source after at least some translations of the position of the ion beam in the second direction in the two-dimensional exposure pattern.

8. The method of claim 1, wherein the one or more mass tags comprise at least one type of antibody-conjugated lanthanide element, and wherein the at least some of the secondary ions comprise at least one type of lanthanide ion.

9. A system, comprising:
an ion source configured to generate an ion beam;
a stage positioned to support a biological sample;
an ion detector configured to detect ions generated from the sample; and
a controller connected to the ion source, the stage, and the ion detector, and configured so that during operation, the controller:
directs the ion source to translate a position of the ion beam from a first location to a second location on the sample, wherein the ion beam is incident on the sample at a first angle to a plane of the sample, and wherein the translation comprises displacing the ion beam in a first direction relative to a projection of a direction of incidence of the ion beam on the sample, and in a second direction relative to the projection of the direction of incidence of the ion beam on the sample, wherein an angle between the first direction and the projection of the direction of incidence of the ion beam on the sample is 20 degrees or less and an angle between the second direction and the projection of the direction of incidence of the ion beam on the sample is 70 degrees or more;
adjusts a focal length of the ion source based on the displacement in the first direction but not on the displacement in the second direction;
directs the ion source to expose the sample to the ion beam at the second location;
receives a signal from the ion detector comprising information about secondary ions generated from the sample in response to the ion beam exposure after adjustment of the focal length; and analyzes the signal to determine mass spectral information for the sample, wherein the sample is labeled with one or more mass tags and the mass spectral information comprises populations of the mass tags at locations of the sample.

10. The system of claim 9, wherein the controller is configured to direct the ion source to translate the position of the ion beam on the sample by adjusting an angle of the ion beam relative to an axis of the ion source.

11. The system of claim 9, wherein the controller is configured to direct the ion source to translate the position of the ion beam across the sample in a two-dimensional exposure pattern, wherein a maximum length of the two-dimensional exposure pattern in the first direction is at least 100 microns, and wherein a maximum length of the two-dimensional exposure pattern in the first direction is at least 500 microns.

12. The system of claim 9, wherein the controller is configured to adjust the focal length of the ion source by adjusting a numerical aperture of the ion source.

13. The system of claim 9, wherein the controller is configured to adjust the ion source to reduce spherical aberration of the ion beam on the sample by adjusting voltages applied to one or more electrodes in the ion source.

14. The system of claim 9, wherein the controller is configured to adjust the ion source to compensate for curvature of a focal plane of the ion source by adjusting voltages applied to one or more electrodes in the ion source.

15. The system of claim 11, wherein the controller is configured to adjust the focal length of the ion source after at least some translations of the position of the ion beam in the second direction in the two-dimensional exposure pattern.

* * * * *